United States Patent

Sharkey et al.

[11] Patent Number: 5,823,994
[45] Date of Patent: Oct. 20, 1998

[54] METHOD AND APPARATUS FOR SOFT TISSUE FIXATION

[75] Inventors: Hugh Sharkey, Redwood City; Gary Fanton, Portola Valley, both of Calif.

[73] Assignee: Oratec Interventions, Inc., Menlo Park, Calif.

[21] Appl. No.: 616,752

[22] Filed: Mar. 15, 1996

[51] Int. Cl.$^6$ ........................................ A61M 31/00
[52] U.S. Cl. ........................ 604/60; 604/57; 604/11; 604/15; 604/46
[58] Field of Search ........................ 604/60, 57, 72, 604/11, 15, 46, 158, 161, 164, 171; 606/232, 72, 74, 75, 60, 63, 213, 214, 215, 229

[56] References Cited

U.S. PATENT DOCUMENTS

| | | | |
|---|---|---|---|
| 4,950,234 | 8/1990 | Fujioka et al. | 604/60 |
| 5,284,479 | 2/1994 | de Jong | 604/60 |
| 5,484,403 | 1/1996 | Yoakum et al. | 604/60 X |
| 5,542,920 | 8/1996 | Cherif Cheikh | 604/60 X |

Primary Examiner—Michael Powell Buiz
Assistant Examiner—N. Kent Gring
Attorney, Agent, or Firm—Wilson Sonsini Goodrich & Rosati

[57] ABSTRACT

An apparatus for repairing a wound in soft tissue includes an introducer trocar with a sharpened distal end and a hollow lumen. An elongated pin has a distal end, a proximal end and a central section. The pin is formed of compacted, hydrophilic, cross-linked collagen and introduced into the hollow lumen in a non-deployed state. An advancement member includes a distal end and is at least partially positioned in the hollow lumen. The advancement member advances the elongated pin out of the introducer trocar distal end and into a soft tissue structure in the pin's non-deployed state and across a wound in the soft tissue structure. The pin becomes deployed to a deployed state when the collagen in the pin begins to hydrolyze, anchoring the pin and the wound so that the wound can be healed quickly. This produces a maintenance of position for two non-continuous bodies of soft tissue relative to each other. The non-continuity may be the result of a wound, laceration, cut or tear in contiguous soft tissue or at a location where approximation and joining of two discontinues soft tissue structures is desirable.

21 Claims, 5 Drawing Sheets

METHOD AND APPARATUS FOR SOFT TISSUE FIXATION

BACKGROUND OF THE INVENTION

1. Field of the Invention

This invention relates generally an apparatus and method for repairing discontinues bodies in soft tissue, and more particularly to an apparatus and method which utilizes a pin initially made of compacted, hydrophilic cross-linked collagen which upon hydrolysis in the soft tissue becomes expanded and anchored.

2. Description of Related Art

Collagen is the major protein component of bone, cartilage, skin and connective tissue in animals. Collagen in its native form is typically a rigid, rod-shaped molecule approximately 300 nm long and 1.5 nm in diameter. It is composed of three collagen polypeptide which form a tight triple helix. The collagen polypeptide are characterized by a long mid section having repeating sequence Gly-X-Y-, where X and Y are often telopeptide regions, which constitute less than about 5% of the molecule. The telopeptide regions of the collagen chains are typically responsible for the cross-linking between chains, and for the immunogenicity of the protein. Collagen occurs in several "types", having differing physical properties. The most abundant types are Types I, II and III. Type I is the major portion of both soft and hard connective tissue. Type II collagen is the major collagen of cartilage. Type III is found in blood vessels, fetal membranes and wounds.

Injectable bovine collagen has been marketed for soft tissue augmentation since the early 1980's. This collagen is derived from bovine hide and is prepared by solubilizing the hide in acid, proteolytically digesting the soluble collagen to remove telopeptides, and purifying the atelopeptide collagen. The collagen is subsequently sterilized by submicron filtration and then reconstituted. Two forms of this collagen, one uncross-linked and the other lightly cross-linked, are currently marketed under the trademarks ZYDERM and ZYPLAST, respectively. Both forms comprise about 95% type I collagen and 5% type III collagen.

The use of collagen compositions for tissue repair and augmentation is known. The collagen may be utilized in a variety of forms, including cross-linked and non-cross-linked fibrillar collagens, gelatins, and the like, and may be combined with various other components, such as lubricants, osteogenic factors, ceramic particles, and the like, depending on the intended use. For soft tissue repair, suspensions of fibrillar collagen have often been used by injecting the composition to a treatment site through a fine gauge needle. For bone and hard tissue repair, fibrillar collagens have been combined with ceramic powders, such as hydroxyapatite and other calcium phosphates.

Collagen is typically isolated from natural sources, such as bovine hide, cartilage or bones. Bones are usually dried, defatted, crushed and demineralized to extract collagen, while hide and cartilage are usually minced and digested with proteolytic enzymes, other than collagenase. As collagen is resistant to most proteolytic enzymes, this procedure conveniently serves to remove most of the contaminating protein found with collagen. Collagen may be denaturized by boiling, which produces the familiar product gelatin.

Human collagen has been proposed as a biomaterial for numerous indications, including soft tissue augmentation. Human collagen has the advantage of being less immunogenic than bovine-derived collagen. It has the disadvantage of requiring additional processing steps to ensure the elimination of human pathogens such as viruses.

The treatment of discontinues bodies in soft tissue, such as a tear in the meniscus of the knee has previously involved primary surgical repair using arthroscopy. In the meniscus, the surgical repair technique requires the passage of sutures and surgical needles through the knee capsule which are tied externally. There are a number of drawbacks to this procedure, including the need for an accessory incision in the back of the knee, potential injury to the nerves and blood vessels by passing the needle through the knee, as well as the additional time and advanced skills required.

A need exists for a collagen pin for soft tissue repair. There is a further need for a collagen pin that is inserted in soft tissue, becomes anchored in the soft tissue in order retain a wound in the soft tissue in a fixed position and permit anastomosis to occur across the wound.

SUMMARY OF THE INVENTION

Accordingly, it is an object of the present invention to provide an apparatus for soft tissue repair that includes a collagen pin.

Another object of the present invention is to provide an apparatus for repairing a wound in soft tissue which introduces one or more collagen pins across a wound in soft tissue.

A further object of the present invention is to provide an apparatus for repairing a wound in soft tissue with one or more collagen pins, where each collagen pin has a central section and proximal and distal ends which have larger cross-sectional dimensions than the cross-section of the central section.

Yet another object of the present invention is to provide an apparatus for repairing a wound in soft tissue with one or more dry, cross-linked collagen pins.

Another object of the present invention is to provide an apparatus for repairing wounds in soft tissue with one or more collagen pins that are positioned across the wound, effecting an anchoring of the wound so that it heals.

A further object of the present invention is to provide a method for repairing a wound in soft tissue by inserting a collagen pin across the wound.

Yet another object of the present invention is to provide a method for repairing a wound in the meniscus of the knee by positioning one or more collagen pins across the wound.

This and other objects of the present invention are achieved in an apparatus for repairing a wound in soft tissue which includes an introducer trocar with a sharpened distal end and a hollow lumen. An elongated pin has a distal end, a proximal end and a central section. The pin is formed of compacted, hydrophilic, cross-linked collagen and introduced into the hollow lumen in a non-deployed state. An advancement member includes a distal end and is at least partially positioned in the hollow lumen. The advancement member advances the elongated pin out of the introducer trocar distal end and into a soft tissue structure in the pin's non-deployed state and across a wound in the soft tissue structure. The pin becomes deployed to a deployed state (transforms from the non-deployed state to the deployed state) when the collagen in the pin begins to hydrolyze, anchoring the pin and the wound so that the wound can be healed quickly.

The present invention also provides a method of repairing a wound in collagen soft tissue. A pin made of compressed collagen in a non-deployed state with a proximal end, a distal end, and a central section is provided and introduced into a selected soft tissue site. The pin is advanced in the soft tissue to a position where the pin's distal end is on a first side of the wound, the pin's proximal end is on a second side of the wound and the pin's central section extends across the wound. The pin is expanded in the soft tissue to a deployed state and the pins's distal and proximal ends become anchored in the soft tissue.

The pin's distal and proximal ends preferably have larger cross-sectional diameters than a diameter of the pin's central section. The pin is made of a compacted, rolled sheet of hydrophilic collagen. Each end of the pin can have a different geometry including but not limited to cylindrical, conical and the like. Additionally, the pin's distal end and proximal ends can have different geometric configurations and sizes.

The apparatus of the present invention can be used to repair a wound in a variety of different soft tissues, including but not limited to the meniscus of the knee.

DETAILED DESCRIPTION

For purposes of this specification, a wound is defined to include a wound, cut, laceration or area between two discontinues bodies in tissue. Hydrophilic, cross-linked collagen is dry enough so that when it is introduced to a desired tissue site in a non-deployed configuration, it begins to hydrolyze, expands and then anchors in the tissue site. The degree of hydrophilic behavior is dependent on the application, the tissue site and the degree of deployment desired. The present invention is suitable for use with a variety of wounds including but not limited to repairs of the knee meniscus. In the setting of the meniscus, healing is promoted because the body of the pin traverses the non-vascularized "white" portion of the meniscus and extends in to the "pink" portion which is increasingly vascularized as you proceed laterally. Establishing a communicating channel between these two zones allows for the flow of serous fluids from the vascularized pink section to the non-vascularized white section which promotes heating of the lesion 1. The collagen pin acts as a wick for the fluids and continuously reestablishes the channel as it is reabsorbed by the body.

This pin could also be a rolled web matrix and a hollow cone that would communicate these fluids down the central core and allow passage of serous fluids through the walls.

Figure 1:
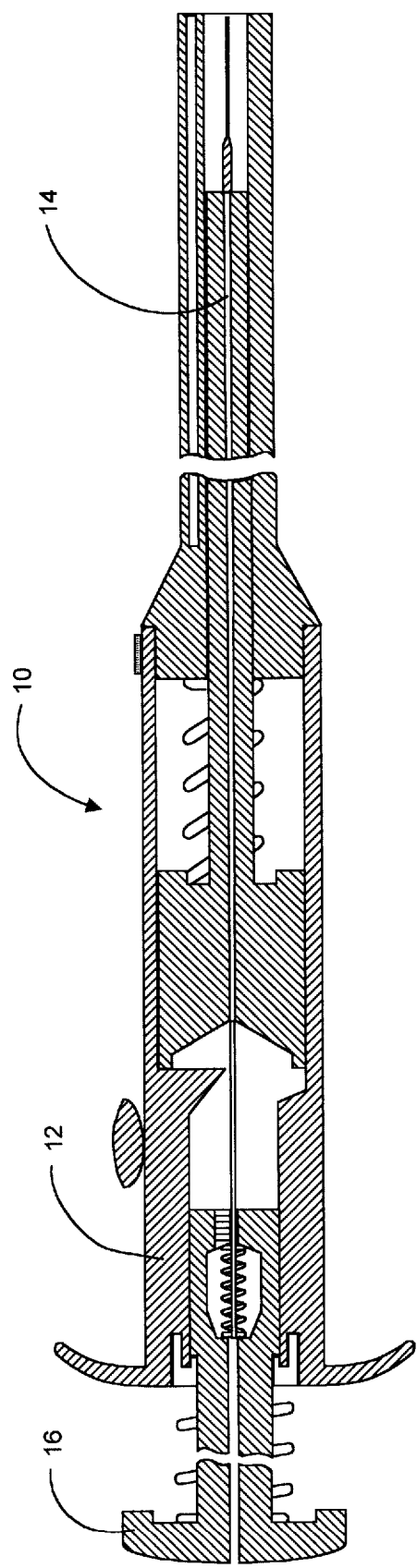
FIG. 1 is a cross-sectional view of a soft tissue fixation pin apparatus.

Referring now to FIG. 1, a soft tissue fixation pin apparatus 10 includes an introducer trocar 12 with a hollow lumen. An elongated pin 14 with a distal end 14', a proximal end 14" and a central section 14'" is positioned in the hollow lumen. Pin 14 is formed of hydrophilic, cross-linked collagen and introduced into the hollow lumen in a non-deployed state. An advancement member 16 has a distal end 16' that is at least partially positioned in the hollow lumen. Advancement member 16 advances elongated pin 14, in a non-deployed state, out of introducer trocar 12 into a soft tissue and across two discontiguous structures in the soft tissue, including but not limited to a wound, cut, tear, laceration, two discontinues tissue section, and the like, hereafter collectively referred to as a ("wound"). Upon hydrolysis after insertion to the desired wound, pin 14 is in an enlarged deployed state. The hydrolyzed collagen becomes anchored in the soft tissue resulting in pin 14 and the wound becoming anchored. When the wound is anchored the wound is substantially immobilized and the healing can then proceed in a quicker fashion.

Figure 2:
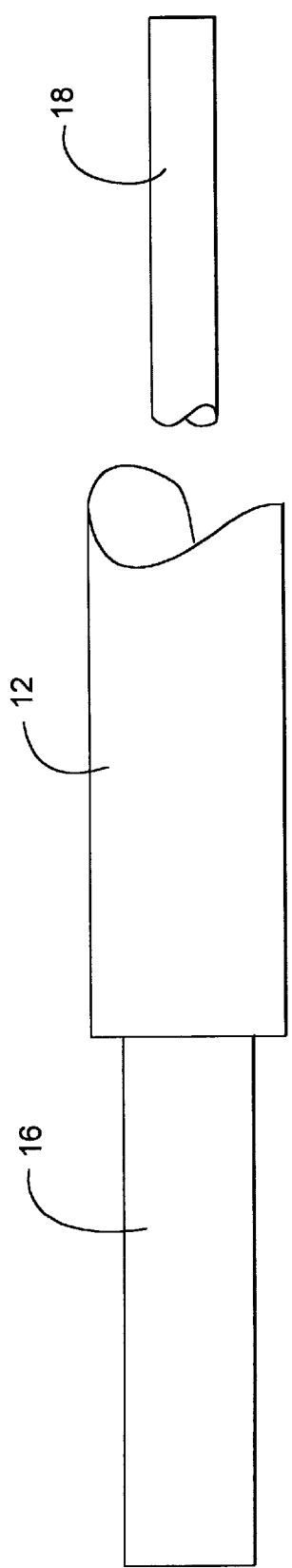
FIG. 2 is a schematic diagram of an actuator used with the apparatus of FIG. 1.

Distal end 12' of introducer trocar 12 can have a sharpened tip in order to be inserted into the soft tissue. As illustrated in FIG. 2, apparatus 10 can further include a flexible tip 18 which may be an integral or connectable element of introducer trocar 12. Flexible tip 18 may be oriented in a desired direction of the wound under treatment after insertion into the soft tissue. Pin 14 is positioned in flexible tip 18 and is driven out of distal end 12' by actuator 16. Actuator 16 is operated outside of the soft tissue.

Figure 3:
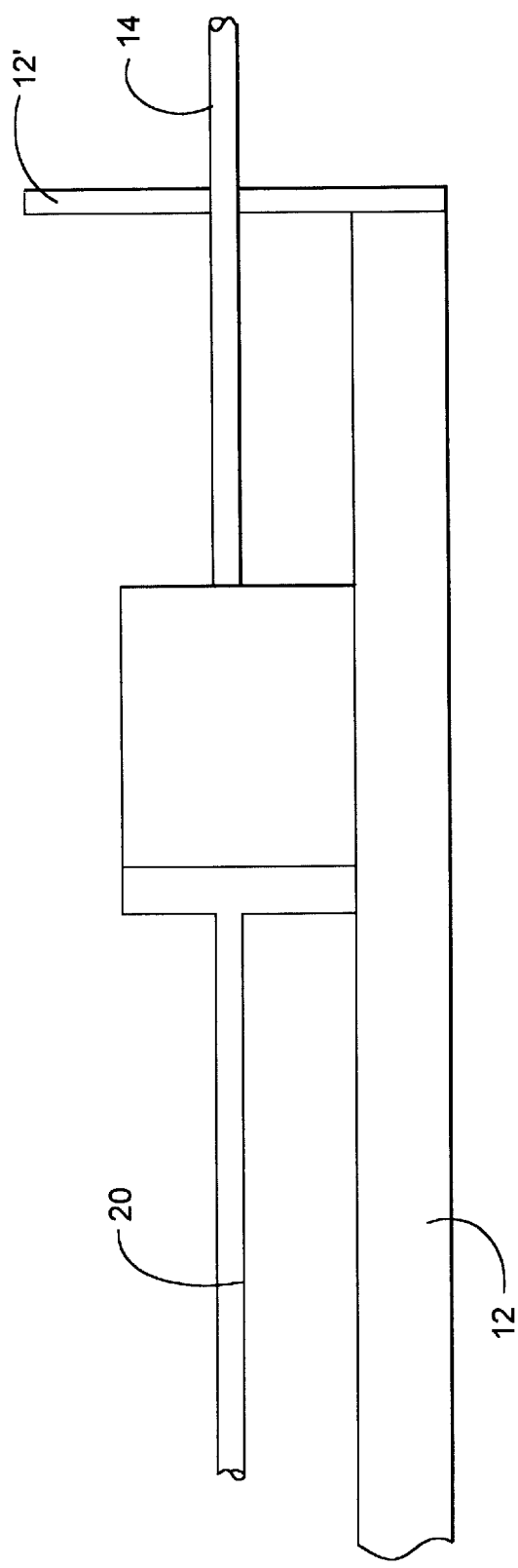
FIG. 3 is a cross-sectional view of a distal end of the soft tissue fixation pin in an embodiment that includes a flexible tip.

Referring now to FIG. 3, flexible tip 18 is distal end 12' of introducer trocar 12 which includes the hollow lumen. Actuator 16 extends through the lumen. Actuator 16 may also have a central lumen through which a guide wire or needle 20 extends. Needle 20 can be utilized to introduce a variety of different materials into a lumen formed in pin 14, as more fully explained hereafter. A distal end of guide wire 20 pushes against pin 14 in order to advance its movement out of introducer trocar 12.

Actuator 16 can include a pair of scissors arms which pivot and advance a body of actuator 16. Further, actuator 16 may include a plunger which is in direct mechanical contact with the body of actuator 16.

Figure 4:
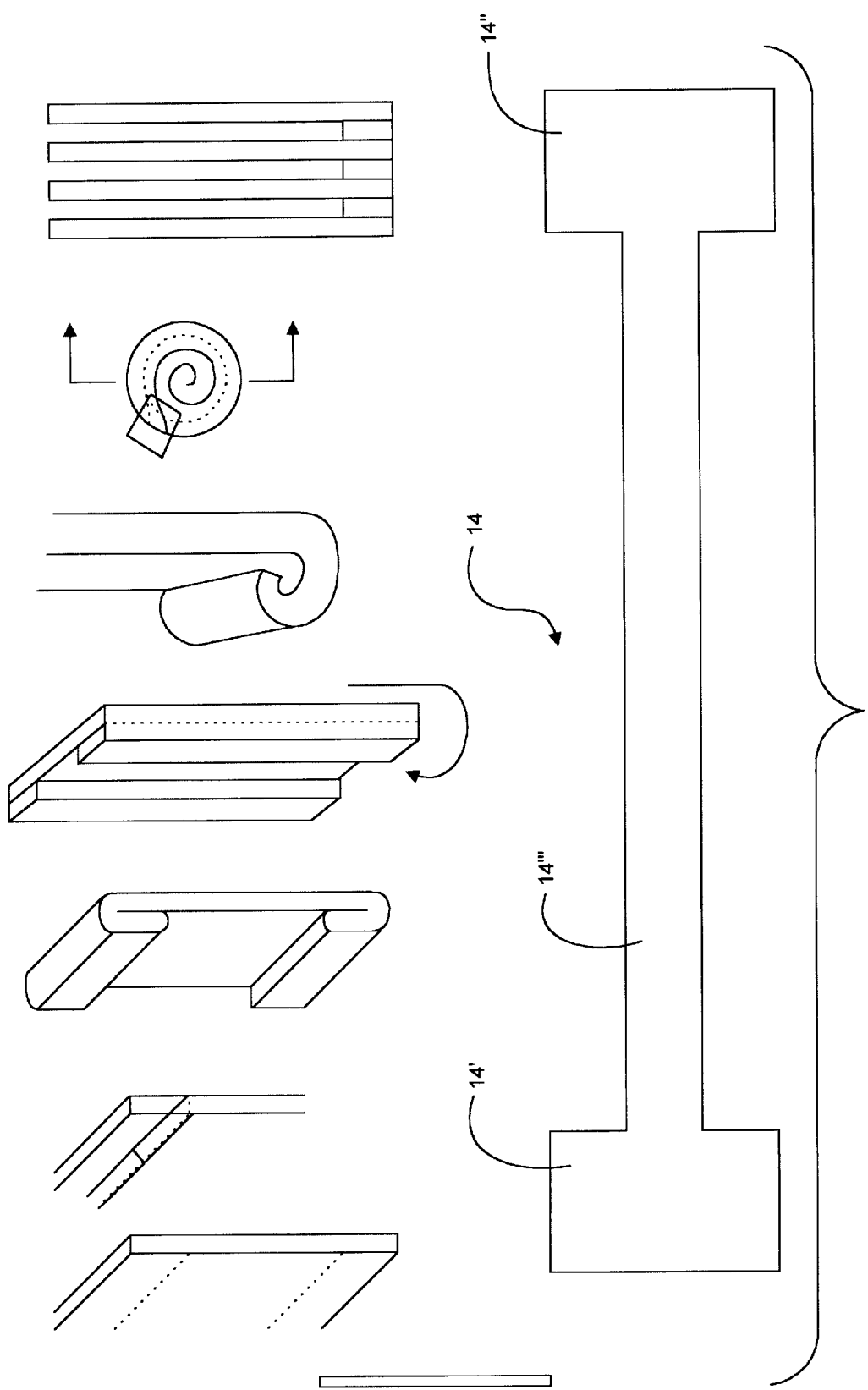
FIG. 4 is a schematic diagram of the collagen pin of the apparatus of FIG. 1.

As illustrated in FIG. 4, pin 14 includes a distal end 14', a proximal end 14" and a central section 14'". In one embodiment, distal and proximal ends 14' and 14" have larger cross-section diameters than central section 14'". In another embodiment the cross-section diameters are all the same size. Still in a further embodiment, distal and proximal ends 14' and 14" do not have the same cross-section diameters, but each is still larger than the cross-section diameter of central section 14'". As shown in FIG. 4 distal and proximal ends 14' and 14" have cylindrical geometric configurations. Other geometric configurations are possible including but not limited to conical, irregular shapes, rectangular, cubic and the like. Distal and proximal ends 14' and 14" may have the same or different geometric configurations.

Figure 5:
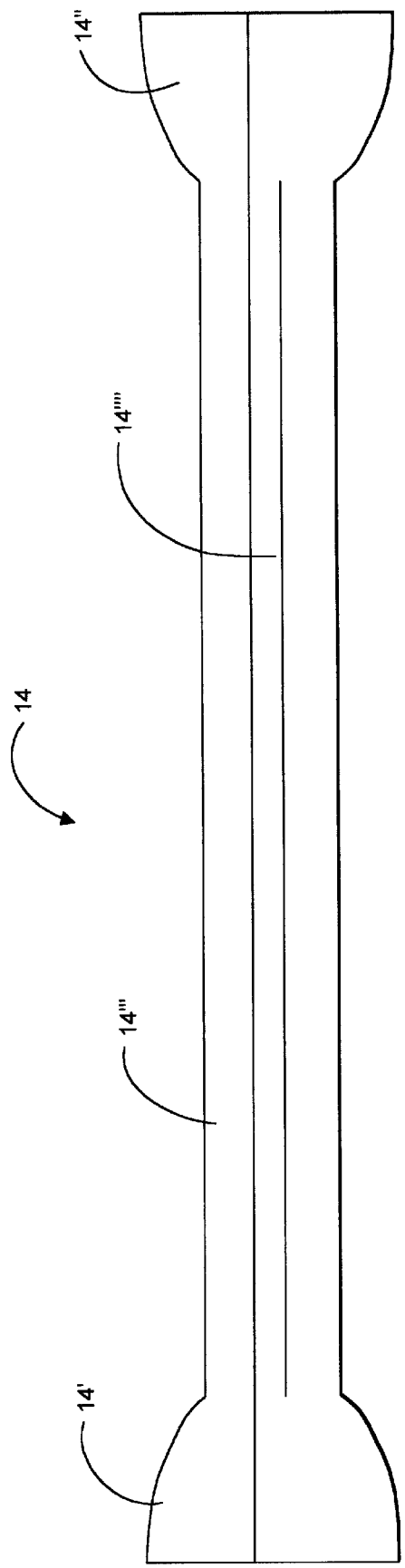
FIG. 5 is a cross-sectional view of a collagen pin with a central lumen.

Referring now to FIG. 5, pin 14 can include a central lumen 14"" which provides access through a needle to inject liquid collagen or other hydraulic agent to expand pin 14 segmentally after softening. Central lumen 14"" need not extend to distal and proximal ends 14' and 14". Additionally, central lumen 14"" may be hollow to promote the incursion of serous fluids across the length of the channel. A central core of pin 14 can be composed of an absorbable material with different tensile properties for improved strength, in order to impact greater longitudinal sheer strength a core pin of another material, i.e., PGA or some other bio-absorbable yet not hydrophilic material could be used as the central core to prevent shearing of the pin across its length.

The operation of soft tissue fixation pin apparatus 10 is now discussed as it is used for the repair of the knee meniscus. It will be appreciated, however, that the present invention is not limited to the knee meniscus. In operation distal end 12' is advanced into the knee and across the two segments of the meniscus. Pin 14 is then advanced out of introducer trocar 12 while introducer trocar 12 is retracted from the surgical site. Additionally, pin 14 can be introduced across the wound once introducer trocar 12 has been removed.

When a guidewire or needle is included, distal end 12' or flexible tip 18 is inserted into the central portion of a patient's knee. Guidewire 20 or distal end 12' crosses the meniscal wound under treatment and forms a channel for pin 14. Pin 14 is then driven across the wound in a non-deployed, compacted state.

Pin 14 is introduced into the selected tissue site. A distal end 14' of pin 14 is at a first side of a wound and a proximal end 14" is on a second side of the wound. Central section 14'" extends across the wound. Pin 14 then becomes expanded in the soft tissue to a deployed state when the collagen begins to hydrolyze. Distal and proximal ends 14' and 14" become anchored in the soft tissue. This retains the wound so that its two sides become immobilized.

Figures 6A, 6B, 6C:
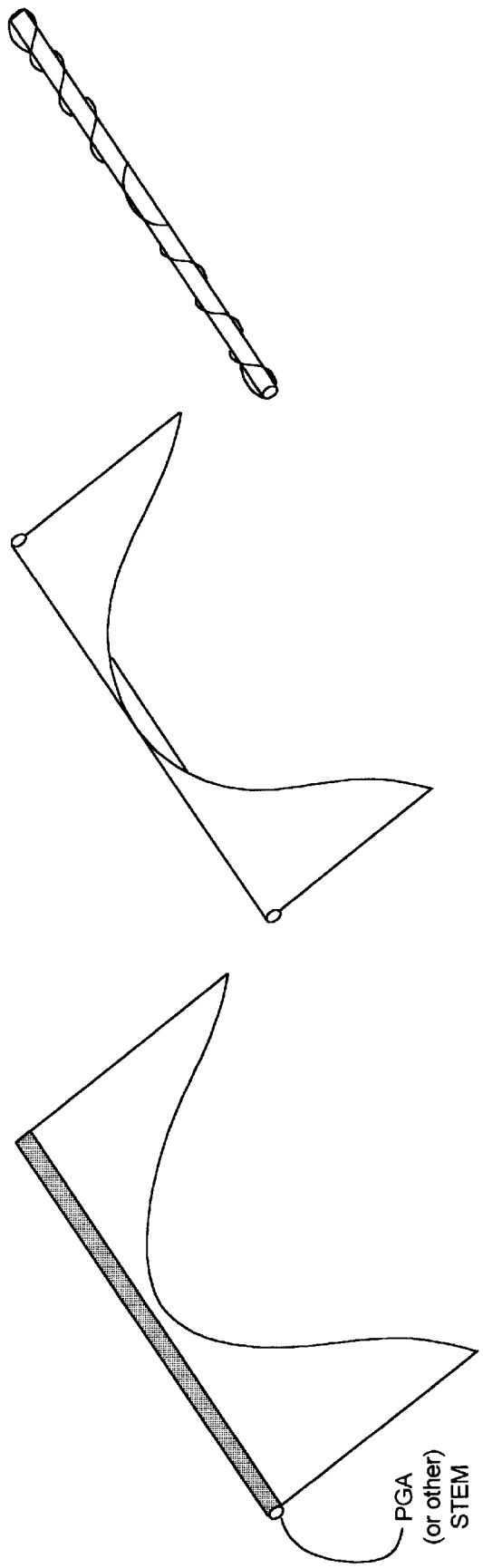
FIGS. 6(a) through 6(c) illustrate a thin layer of collagen that is rolled together to form the collagen pin.

As illustrated in FIGS. 6(a) through 6(c), in one embodiment of the invention the dried collagen may be presented in a rolled configuration.

FIG. 6A shows the configuration of a film or sheet of collagen around a PGA stem or core that is the rolled up tight in its dry form. When exposed to the fluids in the joint and the ends with their greater mass of hydrophilic material (collagen) will expand to a much greater degree than the central shaft thereby creating a mechanical grip forcing the material on either side of the defect to remain together.

Biocompatible human or bovine derived collagen can be used to make pin 14. Suitable collagen compositions with cross-linking agents are disclosed in U.S. Pat. No. 4,061,787, incorporated herein by reference. Cross-linked compositions for the pin 14 may be in the form of a dehydrated particulate material. A method for making dry collagen is disclosed in U.S. Pat. No. 4,442,655, incorporated herein by reference.

The collagen used to make pin 14 may be mixed with minerals, bone marrow or other particulate materials for use in hard tissue augmentation repair, including but not limited to bone, cartilage or dental repair, as described in U.S. Pat. Nos. 4,743,229; 4,776,890; 4,775,467; 4,774,227; and 4,789,663, all incorporated herein by reference. In one embodiment, the collagen utilized is human collagen.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A soft tissue fixation pin apparatus, comprising:
an introducer trocar with a hollow lumen;
an elongated pin located in the hollow lumen, the elongated pin including a distal end, a proximal end and a central section, the elongated pin including a hydrophilic, cross-linked collagen and being introduced into the hollow lumen in a non-deployed state; and an advancement member with a distal end and at least partially positioned in the hollow lumen, wherein the advancement member advances the elongated pin out of the introducer trocar distal end and into a soft tissue structure in the non-deployed state and across a wound in the soft tissue structure, wherein the elongated pin transforms in shape from the non-deployed state to an enlarged deployed state when the hydrophilic, cross-linked collagen in the elongated pin begins to hydrolyze.

2. The apparatus of claim 1, wherein both the distal end and the proximal end each have a larger cross-section diameter than a diameter of the central section.

3. The apparatus of claim 1, wherein the elongated pin includes a compacted, rolled sheet of hydrophilic collagen.

4. The apparatus of claim 1, wherein the distal end and the proximal end each have a cylindrical geometric configuration.

5. The apparatus of claim 1, wherein the distal end and the proximal end each have a conical geometric configuration.

6. The apparatus of claim 1, wherein the distal end and the proximal end each have a different geometric configuration.

7. The apparatus of claim 1, wherein the distal end and the proximal end are substantially the same size.

8. The apparatus of claim 1, wherein the distal end and the proximal end are each different sizes.

9. The apparatus of claim 1, wherein the cross-section dimension of the elongated pin in the non-deployed state is no more than 4 Fr.

10. The apparatus of claim 1, wherein the cross-section dimension of the elongated pin in the non-deployed state is from 0.4 to 0.06 inches.

11. The apparatus of claim 1, wherein a density of the hydrophilic cross-linked collagen is less in the central section than in either the proximal end or the distal end.

12. The apparatus of claim 1, wherein the elongated pin includes a lumen made of an absorbable material that has a different tensile property than a remainder of the elongated pin.

13. A method of repairing a wound in a soft tissue site, comprising:
providing a pin in a non-deployed state with a proximal end, a distal end, and at central section, said pin including a compressed collagen;
introducing the pin into a selected soft tissue site;
advancing the pin in the selected soft tissue site to a position where the distal end is on a first side of the wound, the proximal end is on a second side of the wound, and the central section extends across the wound;
hydrolyzing the compressed collagen to transform the shape of the pin in the soft tissue from the non-deployed state to an expanded deployed state; and
anchoring the distal end and the proximal end in the selected soft tissue site.

14. The method of claim 13, wherein the step of providing includes providing pin that includes hydrophilic collagen.

15. The method of claim 13, wherein the step of providing includes providing a pin wherein a cross section of each of the distal end and proximal end is larger than a cross section of the central section.

16. The method of claim 13, wherein the pin is positioned in an introducer trocar, the introducer trocar having a sharpened distal end, before the pin is introduced into the selected soft tissue site.

17. The method of claim 13, wherein the pin becomes deployed to its deployed state after the pin is introduced into the selected soft tissue site.

18. The method of claim 13, wherein the first side and the second side become anchored.

19. The method of claim 13, wherein the soft tissue is a meniscus of the knee.

20. The method of claim 13, wherein the step of providing includes providing the pin with a central cone made of an absorbable material with a different tensile property than a remainder of the pin.

21. The method of claim 13, wherein the step of providing includes providing the pin with a hollow lumen that promotes the incursion of serus fluid across a length of a serus channel.

* * * * *

UNITED STATES PATENT AND TRADEMARK OFFICE
CERTIFICATE OF CORRECTION

PATENT NO. : 5,823,994
DATED : October 20, 1998
INVENTOR(S) : Sharkey, et al.

It is certified that error appears in the above-identified patent and that said Letters Patent is hereby corrected as shown below:

Column 6, line 59, "providing pin" should be --providing a pin--.

Signed and Sealed this

Sixteenth Day of February, 1999

Attest:

Attesting Officer

Acting Commissioner of Patents and Trademarks

UNITED STATES PATENT AND TRADEMARK OFFICE
CERTIFICATE OF CORRECTION

PATENT NO. : 5,823,994
DATED : October 20, 1998
INVENTOR(S) : Sharkey, et al.

It is certified that error appears in the above-identified patent and that said Letters Patent is hereby corrected as shown below:

Column 1, on or around printer line number 8, "discontinues" should be --discontinuous--.

Column 2, on or around printer line number 4, "discontinues" should be --discontinuous--.

Column 3, on or around printer line 15, "end" should be --and--.

Column 3, on or around printer line 40-41, "discontinues bodies in tissue" should be --discontinuous bodies of tissue--.

Column 4, on or around printer line 12, "hydrolyzed" should be --hydrated--.

Column 4, on or around printer line 9, "discontinues tissue section" should be --discontinuous tissue sections--.

UNITED STATES PATENT AND TRADEMARK OFFICE
CERTIFICATE OF CORRECTION

PATENT NO. : 5,823,994
DATED : October 20, 1998
INVENTOR(S) : Sharkey, et al.

It is certified that error appears in the above-identified patent and that said Letters Patent is hereby corrected as shown below:

Column 4, on or around printer line 11, "hydrolysis" should be --hydration--.

Column 4, on or around printer line 57, "hydraulic" should be --hydrating--.

Column 4, on or around printer line 63, "strength, in" should be --strength. In--.

Column 5, on or around printer line 22, "hydrolyze" should be --hydrate--.

Column 6, on or around printer line 10, "hydrolyze" should be --hydrate--.

Column 6, on or around printer line 44, "and at central" should be --and a central--.

Signed and Sealed this

Twenty-ninth Day of June, 1999

Attest:

*Attesting Officer*

Q. TODD DICKINSON

*Acting Commissioner of Patents and Trademarks*